US012297170B2

(12) United States Patent
Krill (10) Patent No.: US 12,297,170 B2
(45) Date of Patent: May 13, 2025

(54) SIMPLIFIED WORKUP OF THE REACTOR OUTPUT FROM AN OXIDATIVE ESTERIFICATION

(71) Applicant: RÖHM GMBH, Darmstadt (DE)

(72) Inventor: Steffen Krill, Muehltal (DE)

(73) Assignee: Röhm GmbH, Darmstadt (DE)

( * ) Notice: Subject to any disclaimer, the term of this patent is extended or adjusted under 35 U.S.C. 154(b) by 596 days.

(21) Appl. No.: 17/753,245

(22) PCT Filed: Aug. 20, 2020

(86) PCT No.: PCT/EP2020/073321
§ 371 (c)(1),
(2) Date: Feb. 24, 2022

(87) PCT Pub. No.: WO2021/037660
PCT Pub. Date: Mar. 4, 2021

(65) Prior Publication Data
US 2022/0363625 A1    Nov. 17, 2022

(30) Foreign Application Priority Data

Aug. 28, 2019    (EP) .................................... 19193981

(51) Int. Cl.
*C07C 67/44*    (2006.01)
*C07C 67/54*    (2006.01)

(52) U.S. Cl.
CPC ............. *C07C 67/44* (2013.01); *C07C 67/54* (2013.01)

(58) Field of Classification Search
CPC ......... C07C 67/44; C07C 67/54; C07C 67/39; C07C 67/58; C07C 69/54
See application file for complete search history.

(56) References Cited

U.S. PATENT DOCUMENTS 5,969,178 A    10/1999    Okamoto et al.
7,012,039 B2    3/2006    Watanabe et al.
(Continued)

FOREIGN PATENT DOCUMENTS

CN    108440281    8/2018
EP    0194620    9/1986
(Continued)

OTHER PUBLICATIONS

International Search Report issued Nov. 5, 2020 in PCT/EP2020/073321, with English translation, 5 pages.
(Continued)

*Primary Examiner* — Jafar F Parsa
(74) *Attorney, Agent, or Firm* — Grüneberg and Myers PLLC (57) ABSTRACT

A process can be used for preparing methyl methacrylate by direct oxidative esterification of methacrolein. Methyl methacrylate is used in large amounts for preparing polymers and copolymers with other polymerizable compounds. In addition, methyl methacrylate is an important synthesis unit for a variety of specialty esters based on methacrylic acid (MAA) which can be prepared by transesterification with the appropriate alcohol. There is consequently a great interest in very simple, economic and environmentally friendly processes for preparing this starting material. A corresponding optimized workup of the reactor output from the oxidative esterification of methacrolein, through which unconverted methacrolein (MAL) can be recycled very efficiently, is useful. In addition, the process can be carried out in a manner which compared to known variants is markedly more energy- and water-saving.

16 Claims, 4 Drawing Sheets

(56) References Cited

U.S. PATENT DOCUMENTS

| | | |
|---|---|---|
| 9,617,199 B2 | 4/2017 | Krill et al. |
| 9,890,105 B2 | 2/2018 | Krill et al. |
| 10,301,251 B2 | 5/2019 | Groemping et al. |
| 10,479,754 B2 | 11/2019 | Krill et al. |
| 11,124,471 B2 | 9/2021 | Lygin et al. |
| 2016/0068464 A1 | 3/2016 | Krill et al. |
| 2016/0251301 A1 | 9/2016 | Krill et al. |
| 2018/0251418 A1 | 9/2018 | Krill et al. |
| 2018/0251419 A1 | 9/2018 | Groemping et al. |
| 2021/0032386 A1 | 2/2021 | Krill et al. |
| 2021/0047259 A1 | 2/2021 | Lygin et al. |
| 2021/0269385 A1 | 9/2021 | Krill et al. |

FOREIGN PATENT DOCUMENTS

| | | |
|---|---|---|
| EP | 3350153 | 6/2019 |
| WO | 2014/170223 | 10/2014 |
| WO | 2017/046110 | 3/2017 |

OTHER PUBLICATIONS

Written Opinion issued Nov. 5, 2020 in PCT/EP2020/073321, with English translation, 12 pages.

U.S. Appl. No. 16/637,575, filed Feb. 7, 2020, 2021/0032386, Krill et al.

U.S. Appl. No. 17/250,260, filed Dec. 22, 2020, 2021/0269385, Krill et al.

| Stream (see list of reference numerals) | | (14)+(6)+(22) | (12) | (11) | (14) | (17) | (20) | (22) | (24) | (25) | (25)+(31)+(38) | (27) | (28) | (32) | (35) | (37) |
|---|---|---|---|---|---|---|---|---|---|---|---|---|---|---|---|---|
| Mass flow rate | kg/h | 44.9 | 53.5 | 11.3 | 4.7 | 90.1 | 72.2 | 27.8 | 7.9 | 22.2 | 24.4 | 1.5 | 22.8 | 1.1 | 17.6 | 15.9 |
| Proportions by mass | | | | | | | | | | | | | | | | |
| N2 | % by wt. | | | 94.4 | | | | | | | | | | | | |
| O2 | % by wt. | | | 4.5 | | | | | | | | | | | | |
| FOME | % by wt. | | | 0.6 | | | | | | | | | | | | |
| MeOH | % by wt. | 55.3 | 46.3 | 0.2 | | 27.5 | 34.1 | 88.7 | <0.1 | 0.9 | 0.8 | | 0.9 | | | |
| MAL | % by wt. | 37.5 | 9.4 | 0.2 | 82.7 | 5.6 | 1.5 | 4.0 | | 17.8 | 16.1 | | 17.2 | | | |
| H2O | % by wt. | 1.5 | 7.7 | | | 44.0 | 60.2 | 0.9 | 97.3 | 2.0 | 1.8 | | 1.8 | | | |
| MMA | % by wt. | 3.4 | 32.4 | | 7.1 | 19.2 | 1.7 | 4.3 | | 72.6 | 75.1 | 30.0 | 78.3 | 1.4 | 99.94 | 99.96 |
| MAL-ACET | PPM | | 361 | | | 1 | | | | | | | | | | |
| MAA | % by wt. | | 0.3 | | | 0.5 | 0.2 | | | 1.6 | 1.5 | 22.9 | | 32.9 | | |
| Na-MAA | % by wt. | | 0.5 | | | | | | | | | 20.0 | | 29.1 | | |
| MMIB | % by wt. | | 0.7 | | | 0.5 | | | | | | | | | | |
| MIB | % by wt. | | | | | | | | | | 0.2 | | 0.2 | | | |
| NA2SO4 | % by wt. | | | | | | 1.4 | | 2.2 | | | | | | | |
| Remainder | % by wt. | 2.3 | 2.6 | | 10.2 | 2.6 | 0.9 | 2.1 | 0.5 | 5.1 | 4.4 | 27.1 | 1.4 | 36.6 | 0.06 | 0.04 |

SIMPLIFIED WORKUP OF THE REACTOR OUTPUT FROM AN OXIDATIVE ESTERIFICATION

CROSS-REFERENCE TO RELATED APPLICATIONS

This application is the National Stage entry under § 371 of International Application No. PCT/EP2020/073321, filed on Aug. 20, 2020, and which claims the benefit of priority to European Application No. 19193981.8, filed on Aug. 28, 2019. The content of each of these applications is hereby incorporated by reference in its entirety.

BACKGROUND OF THE INVENTION

Field of the Invention

The present invention relates to a process for preparing methyl methacrylate by direct oxidative esterification of methacrolein. Methyl methacrylate is used in large amounts for preparing polymers and copolymers with other polymerizable compounds. In addition, methyl methacrylate is an important synthesis unit for a variety of specialty esters based on methacrylic acid (MAA) which can be prepared by transesterification with the appropriate alcohol. There is consequently a great interest in very simple, economic and environmentally friendly processes for preparing this starting material.

In particular, the present invention relates to an optimized workup of the reactor output from the oxidative esterification of methacrolein by means of which unconverted methacrolein (MAL) can be recycled very efficiently. In addition, this novel process can be carried out in a manner which compared to known variants is markedly more energy- and water-saving.

Description of Related Art

Methyl methacrylate (MMA) is currently produced by a variety of processes proceeding from $C_2$, $C_3$ or $C_4$ synthesis units. In one of these processes, MMA is obtained by gas-phase oxidation of isobutylene or tert-butanol with atmospheric oxygen over a heterogeneous catalyst to afford methacrolein and subsequent oxidative esterification reaction of methacrolein using methanol. This process, developed by ASAHI, is described, inter alia, in publications U.S. Pat. Nos. 5,969,178 and 7,012,039. A particular disadvantage of this process is a very high energy requirement. In a development of the process the methacrolein is obtained from propanal and formaldehyde in the first stage. Such a process is described in WO 2014/170223.

The process according to the invention also comprises the preparation of methacrolein, preferably in a continuous process and with the specific proviso that a purity and quality of methacrolein are achieved which are acceptable for the downstream reaction step of the direct oxidative esterification of methacrolein to MMA. According to the prior art, various processes and embodiments can be considered for preparing methacrolein which make it possible to carry out the present process according to the invention.

In the preparation of methacrolein by the so-called C2 process, the target product is obtained from formalin and propionaldehyde in the presence of a secondary amine and an acid, usually an organic acid. The conversion proceeds via a Mannich-like reaction with subsequent liberation of the catalytic secondary amine.

In general, according to this mechanism, condensation of the formalin with propanal is carried out, with water being formally produced as condensation product. The methacrolein (MAL) synthesized in this way can then be converted in a subsequent step to methacrylic acid by gas-phase oxidation or to methyl methacrylate by oxidative esterification. Such processes for the preparation of methacrolein are described, inter alia, in the publications U.S. Pat. No. 7,141,702. U.S. Pat. No. 4,408,079, JP 3069420, JP 4173757, EP 0 317 909 and U.S. Pat. No. 2,848,499.

The processes based on a Mannich reaction and suitable for the preparation of methacrolein are known to those skilled in the art in general and are the subject of corresponding review articles, for example in Ullmann's Encyclopedia of Industrial Chemistry, 2012. Wiley-VCH Verlag GmbH & Co. KGaA, Weinheim. Acrolein and Methacrolein, DOI: 10.1002/14356007.a01_149.pub2 Embodiments for producing methacrolein from propanal and formalin which are not performed in the presence of amines as catalysts are also known, for example the gas-phase preparation in the presence of fixed-bed catalysts, as most recently publicized by Eastman.

For economic utilization of this process, a high yield and a low specific energy requirement should be attained. According to the teaching of EP 0 194 620, a low content of dimeric methacrolein (DIMAL) in the product, preferably less than 0.2% by weight, and a propionaldehyde content (propanal) of less than 1% by weight should be sought, in order to avoid lasting damage to the oxidation catalyst of an optionally subsequent heterogeneous gas phase catalysis. DE 3213681 describes a process for preparing MAL, which is especially characterized in that the reaction is conducted at a temperature of greater than 150° C. with a reaction time of not more than 25 min in the presence of secondary amines and optionally of acids. In the best case, this involves reacting propionaldehyde with formalin at temperatures of 162 to 205° C. and with a residence time of 6 seconds.

In a further embodiment of DE 3213681, the reactor is operated at an inlet temperature of 161° C. and the temperature increases up to 184'C due to the strongly exothermic reaction. The residence time is approx. 6.9 sec. The water content in the feed to the reaction is approx 50% by weight. The amine content based on the water is 1.8% by weight. For instance, a DIMAL content of 0.29% by weight is observed at a yield of 98.1% using such a process variant.

U.S. Pat. No. 4,408,079 describes a process for preparing MAL in which the reaction of propionaldehyde with formalin is conducted at a molar ratio of 0.9 to 1.5:1, a pH between 2.5 and 7 and temperatures of 0° C. to 150° C. in the presence of a secondary amine, at a concentration of 0.025 to 0.75 or of 0.05 to 1.5 mol, and organic acids at a concentration of 0.05 to 1.5 mol, based in each case on 1 mol of propionaldehyde. In comparison to the teaching of DE 3213681, the selected temperature range is therefore significantly lower. According to U.S. Pat. No. 4,408,079, the reaction is carried out here continuously in a stirred tank cascade of two to three reactors at very long residence times of the reactants of 10 to 90 min With this embodiment of the process, relatively low yields of 91% to 96% are achieved.

In summary, it can be said that, although all of these processes differ very significantly in residence time, catalyst amount and the type of reactors used, in terms of yield and methacrolein quality they are suitable in principle for being used for a subsequent reaction in accordance with a direct oxidative esterification of the methacrolein to MMA in the liquid phase. It is common to all processes that the preparation of methacrolein by condensation of aqueous formalin solutions with propanal is conducted in one or more reactors (the reactors may be connected together in parallel or in the form of a cascade) and that methacrolein is worked up in such a way that an aqueous phase, containing predominantly the process water and the water content entering the reaction with the formaldehyde, is to a large extent removed. The removal serves the further purpose that the pure methacrolein produced is to the greatest possible extent free from traces of catalyst, since there is the possibility that catalyst residues adversely affect the performance of the downstream DOE catalysts.

The preparation of MMA from methacrolein in what is known as direct oxidative esterification in the liquid phase with air and methanol as reactants has particular importance for the present invention.

U.S. Pat. No. 5,969,178 describes such a process for oxidative conversion of isobutene or tert-butanol to methacrolein and subsequent oxidative esterification to MMA. In this second stage a liquid mixture of methacrolein and methanol with reduced water content is reacted with molecular oxygen and a palladium catalyst, wherein said catalyst is usually in supported form as a palladium-lead catalyst. In a first distillation stage a mixture of methacrolein and methanol is then removed from the crude product of the oxidative esterification below the top of the column while low-boiling constituents are removed overhead. The MMA-containing bottoms product is then passed into a second distillation stage in which an azeotrope of methanol and saturated hydrocarbons is removed overhead. The bottoms product comprising the crude MMA is sent to a further workup while methanol is isolated from the overhead fraction by means of a phase separator and a third distillation column and passed back into the reactor. It is to be borne in mind that the methanol can contain relatively large amounts of water on account of the azeotrope formed and must therefore be sent to a dewatering.

As an alternative to this process, U.S. Pat. No. 5,969,178 discloses workup in only one column wherein in said column it is imperative that the feed be situated above the column bottom. Low-boiling constituents from the reactor output are removed from this column overhead. Remaining in the column bottom is a mixture of crude MMA and water which is to be sent to a further workup. Via a sidestream, the exact position of which must first be determined and is adjustable by addition of various sieve trays, a mixture of methacrolein and methanol intended for returning into the reactor is finally taken off from the column. U.S. Pat. No. 5,969,178 itself indicates that such a process is difficult to perform on account of a variety of azeotropes. Furthermore, methacrylic acid in particular, which is always present as a by-product, plays an important role here. According to this process, despite the silence of U.S. Pat. No. 5,969,178 on this issue, the methacrylic acid would be removed in a manner such that it remains in a phase to be sent for disposal and an isolation would be of only limited attractiveness. However, this results in a fall in the overall yield of methacrylic products of this process.

U.S. Pat. No. 7,012,039 discloses a workup of the reactor output from the oxidative esterification which is somewhat of a departure. Here. In a first distillation stage, methacrolein is distilled overhead via sieve trays and the aqueous, MMA-containing mixture from the bottom is passed into a phase separator. In said phase separator the mixture is adjusted to a pH of about 2 by addition of sulfuric acid. The separation of the sulfuric-acid-acidified water from the organic/oil phase is then effected by means of centrifuging. This oil phase is separated in a further distillation into high-boiling constituents and an MMA-containing phase which is withdrawn overhead. The MMA-containing phase is then separated from low-boiling constituents in a third distillation. This is even followed by a fourth distillation for final purification.

The problem with this process is the sulfuric acid which needs to be added in large amounts and can have corrosive effects on parts of the plant. Accordingly, these parts, such as the phase separator or else the second distillation column in particular, have to be fabricated from suitable materials. Moreover, U.S. Pat. No. 7,012,039 is silent regarding the handling of the simultaneously generated methacrylic acid or the residual methanol remaining in the product. However, it can be assumed that the former is also removed in the distillation stages, while the methanol can only partly be obtained and returned with the methacrolein, while the remainder is probably lost in the third distillation stage.

WO 2014/170223 describes a similar process to U.S. Pat. No. 7,012,039. The only difference is that in the actual reaction the pH is adjusted in a circuit by addition of a methanolic sodium hydroxide solution. This serves, inter alia, to protect the catalyst. Moreover, the removal of the aqueous phase in the phase separation is simpler on account of the salt content. However, another consequence is that the methacrylic acid formed is in the form of sodium salt and is later removed and disposed of with the aqueous phase. Although the free acid is recovered in the variant where sulfuric acid is added in the phase separation, sodium (hydrogen) sulfate is generated which can lead to other problems upon disposal.

EP 3 350 153 describes a process in which unconverted alcohol is removed by distillation from the reactor output from an oxidative esterification of methacrolein and is recycled into the reactor.

All of these processes and workup variants share the common feature that the conversion of the DOE reaction is not complete. There is therefore the need to recycle unconverted methacrolein and excess alcohol, especially excess methanol in the case of the preparation of MMA, in a column which is connected directly downstream of the reactor. The steam and cooling water consumption of this column is immense and thus the column not only consumes large amounts of water but also energy.

In summary, the following aspects of the prior art processes, especially in combination with one another, are in need of improvement:
  maximum yield
  maximum degree of recycling of the unconverted methacrolein and alcohol (methanol)
  minimum content, or reduced content compared to the prior art, of alkyl isobutyrate, especially methyl isobutyrate, in the alkyl methacrylate, especially MMA, produced
  minimum water and energy consumption, and maximum cleanliness of disposal streams or off gases

SUMMARY OF THE INVENTION

Problem

The problem addressed by the present invention in view of the prior art is therefore that of providing a technically improved process for oxidative esterification of methacrolein that is not afflicted with the disadvantages of conventional processes.

A particular problem addressed by the present invention was that of providing an improvement in the workup of the crude product from an oxidative esterification of methacrolein and methanol to afford MMA and thus to improve the overall yield of such a process compared to the prior art.

A further problem addressed was that of, to the greatest possible extent, recycling the greatest possible amount of unconverted reactants or by-products or intermediates formed in the process, in particular methanol, methacrolein and water, and converting them in the process into the target products.

A further problem addressed by the present invention was that of improving the isolation of unconverted reactants, especially methacrolein and the alcohol, from the reactor output from the oxidative esterification in such a way that it can be carried out with less energy required and less cooling water.

A further particular problem addressed was that of providing a process that can be performed with a minimum disposal cost, in particular through reduced generation of organic constituents and acids in the waste stream.

The process shall furthermore be inexpensive, in particular in terms of the materials to be employed for construction of the plant, compared to the prior art.

Solution

The problems are solved by a process for preparing MMA, in which methacrolein is prepared in a first reaction stage in a reactor I and this is oxidatively esterified in a second reaction stage in a reactor II with an alcohol to give an alkyl methacrylate. The process according to the invention is characterized here in that the reactor output from reactor II firstly is separated first into a first phase, containing more than 80% by weight of the alcohol present in the reactor output, and a second phase, containing more than 90% by weight in each case of the alkyl methacrylate and methacrolein (MAL) present in the reactor output. This second phase is subsequently separated first into a third phase, containing high-boiling components, and a fourth phase, containing more than 90% by weight in each case of the alkyl methacrylate and methacrolein (MAL) present in the reactor output. This fourth phase is subsequently separated in a distillation column the predominant portion of the alkyl methacrylate from the predominant portion of the MAL.

DETAILED DESCRIPTION OF THE INVENTION

A large number of possible methods and processes may be used to prepare methacrolein as precursor of the DOE, inter alia various processes depicted in the prior art and proceeding from propionaldehyde and formalin and also established processes proceeding from isobutene or isobutene precursors such as MTBE and tert-butanol, which are conducted in the gas phase as air oxidation in tube bundle reactors over suitable heterogeneous catalysts.

This novel process has particular significance for an implementation in which the alcohol is methanol and the alkyl methacrylate is MMA.

It has proven to be particularly advantageous and energy-saving when the fourth phase is first separated in a phase separator from at least 90% by weight of the water present in the fourth phase, before the predominant portion of the alkyl methacrylate is separated from the predominant portion of the MAL in a distillation column.

It has proven to be particularly preferable for the fourth phase or the organic phase of the fourth phase, after separation from an aqueous phase in a phase separator, to be separated in a distillation column into a low-boiling fraction, containing at least 60% by weight of the MAL from the reactor output, and a high-boiling phase, containing at least 90% by weight of the MMA from the reactor output.

An alternative to this is a variant in which the low-boiling MAL-containing fraction which was obtained from the fourth phase is separated from low-boiling constituents in a further column. The high-boiling fraction of this column obtained in the process, containing at least 60% by weight, preferably at least 70% by weight, of the MAL from the reactor output, is then passed into reactor II or into a mixer or heat exchanger connected upstream of reactor II.

It is very particularly preferable here for the MAL-containing fraction obtained from the fourth phase to first be separated from an aqueous phase in a phase separator prior to the distillative separation of low-boiling constituents and the transfer of the MAL fraction into or upstream of the reactor II. This procedure is particularly preferred when this second phase separator and the first phase separator, which is connected upstream of the distillative separation of the fourth phase, are both used.

The accumulating aqueous phases from the phase separators, which in the event of a plurality of such functional parts may be combined with one another, can be fed to a membrane separation stage prior to final disposal. The remaining, more organic phase can optionally be further distilled in such a way that, depending on the procedure, any MAL, methanol and/or MMA present can be isolated and recycled or fed to the MMA final purification. Depending on the specific composition of this phase, it can also be passed directly into the first distillation after discharge from reactor ii for the isolation of methanol. If the intention is to recover predominantly MAL, the phase can also be passed into one of the phase separators, the distillation column for the final MAL recovery or—preferably—into the distillation column for separation of the second phase into the third and the fourth phase.

With regard to the separation of the reactor output into the first and the second phase, it has proven to be advantageous when the reactor output from reactor II is first admixed in a converter with a strong acid and optionally additional water, prior to carrying out extractive separation of the two phases from one another. The first phase, containing only very little MAL, is subsequently separated in a further distillation column into a phase predominantly containing alcohol and a high-boiling phase, which is disposed of. The phase containing the alcohol is preferably recycled into reactor II.

Particularly preferably, the amount of the strong acid added in this procedure is such that the pH during the extraction is always less than 7, preferably less than/equal to 5, but always greater than/equal to 1. The preferred amount of acid corresponds to an addition amount or concentration which ensures that the materials of the apparatuses do not end up being too expensive and high-alloyed, but also that the desired chemical reactions proceed sufficiently rapidly and completely. Such a particularly preferred pH range is between pH 1.5 to pH 4. A pH of between 2 and 3 usually constitutes an optimal compromise between all desired features.

Various advantages are achieved by the measures according to the invention that, after the removal of the methanol from the reactor output, first high boilers are removed, before the product, in the form of the alkyl methacrylate, and the methacrolein are separated from each other. The particularly preferred performance, prior to the distillation to remove the MAL, of a phase separation for the removal of water additionally amplifies these advantages further. The advantages of the process according to the invention, surprisingly achieved both individually and in particular also in combination with one another, are in particular the following:

The, in particular more effectively configured, recovery of the MAL surprisingly increases the overall yield of such a process compared to the prior art. It was in particular possible to firstly isolate unconverted reactants in the reactor particularly efficiently and hence to implement recycling into the reactor to a high degree. This relates, in addition to methanol and methacrolein, to the isolation of water, which can be partially reused in the workup, in turn reducing the amounts of wastewater from the overall process.

It was also very surprisingly possible with the process according to the invention to reduce the content of alkyl isobutyrate, especially methyl isobutyrate, in the alkyl methacrylate, especially MMA, produced, compared to the prior art. This may possibly be explained by the lower thermal load in the workup of the reactor output up to the removal of MAL.

It was additionally surprising that the problem of improving the isolation of unconverted reactants, especially methacrolein and the alcohol, from the reactor output from the oxidative esterification in such a way that it can be carried out with less required energy and less cooling water can be solved with the process according to the invention, especially augmented in the variant of an interposed phase separator prior to the removal of MAL. In addition, surprisingly, the total amount of the—both aqueous as well as organic—waste streams is surprisingly reduced compared to the prior art.

As an alternative to the process as described in the experimental, further connection setups and sequences of the various distillation columns are conceivable. For example, the organic phase from the extraction ("second phase"), which consists primarily of MMA and methacrolein, can in an advantageous variant first be worked up in the low boiler column, with MMA accumulating in the bottoms of the low boiler column and subsequently being sent to the workup in the high boiler column. Here, MMA in monomer quality accumulates as distillate of the high boiler column; compared to other conceivable connection setups, the MMA purifying column is dispensed with in this variant.

EXPERIMENTAL

1. Continuous Performance of the Preparation of Methacrolein by Condensation of Formalin ("FA") with Propanal Preparation of the Starting Material for the DOE (See 2.a.)

Methacrolein can be prepared continuously in accordance with DE3213881A1. Reaction conditions and yields for Examples 1.1. and 1.2. according to DE321388A1 are presented in Table 1. In these examples, methacrolein is prepared continuously at relatively high temperatures.

Examples 1.3. to 1.19. according to EP2998284A1 likewise describe a continuous process, but at markedly lower temperatures compared to Examples 1.1. and 1.2. In these examples, formalin solutions of different concentrations (37% by weight or 55% by weight) and propionaldehyde are mixed by means of a static mixer (referred to below as aldehyde solution) and the mixture is subsequently heated to the desired temperature (see Table 1) in an oil-heated heat exchanger. A recycle stream from the bottom of the product column adjoining the tubular reactor is mixed with acetic acid and dimethylamine (as 40% solution in water) and is likewise pre-heated to the desired temperature. The pre-heated aldehyde solution and the pre-heated catalyst solution are mixed in a further static mixer. This reactant mixture is then fed to a tubular reactor which is temperature-controlled by means of oil. The reaction is typically conducted at pressures of approx. 35 to 40 bar, in order to prevent outgassing of components in the reaction zone. The product mixture at the outflow of the tubular reactor is depressurized via a valve and enters the product column for the distillation. At the top of this column, after condensation and phase separation, a biphasic mixture of methacrolein and an aqueous phase is obtained. The aqueous phase is fed back to the column as reflux. The organic phase enters the product container. At the bottom of the column, a partial stream is fed back into the reaction as recycle. Another partial stream is discharged as aqueous product into a further product container. The conversions in all examples are above 99.3% and the DIMAL contents achieved are between 0.18% and about 1.4% by weight in the isolated methacrolein.

TABLE 1

| | PA:FO | DMA:PA ACOH:DMA Fresh feed | | Recycle | DMA:PA | $H_2O$ Reactor inlet | $DMA/H_2O$ | Residence time |
|---|---|---|---|---|---|---|---|---|
| | mol/mol | mol % | mol/mol | % | mol % | % | % | sec |
| DE3213681A1, Ex. 1.1. | 1 | 3.7 | 1.08 | — | — | 50 | 1.8 | 6.9 |
| DE3213681A1, Ex. 1.2. | 1 | 3.6 | 1.14 | — | — | 40 | 2.5 | 6 |
| Example 1.3. | 0.99 | 2.50 | 1.09 | 70.5 | 7.8 | 55.6 | 2.74 | 9.30 |
| Example 1.4. | 0.99 | 2.51 | 1.09 | 71.0 | 7.8 | 56.1 | 2.74 | 9.26 |
| Example 1.5. | 0.98 | 2.61 | 1.09 | 71.2 | 8.2 | 54.9 | 2.82 | 9.41 |
| Example 1.6. | 0.96 | 2.51 | 1.09 | 70.1 | 7.7 | 56.5 | 2.71 | 9.21 |
| Example 1.7. | 0.99 | 2.51 | 1.09 | 70.5 | 7.8 | 55.7 | 2.75 | 9.26 |
| Example 1.8. | 0.99 | 2.51 | 1.09 | 70.4 | 7.8 | 55.6 | 2.75 | 9.30 |
| Example 1.9. | 0.98 | 2.50 | 1.09 | 70.5 | 7.7 | 56.0 | 2.72 | 9.22 |
| Example 1.10. | 0.99 | 2.51 | 1.09 | 70.5 | 7.8 | 55.6 | 2.74 | 9.26 |
| Example 1.11. | 0.99 | 2.52 | 1.08 | 70.4 | 7.8 | 55.6 | 2.76 | 9.26 |
| Example 1.12. | 0.99 | 2.50 | 1.09 | 48.8 | 4.7 | 56.4 | 1.76 | 9.23 |

TABLE 1-continued

| | | | | | | | | |
|---|---|---|---|---|---|---|---|---|
| Example 1.13. | 1.01 | 2.49 | 1.10 | 52.8 | 5.2 | 58.4 | 1.73 | 11.26 |
| Example 1.14. | 1.00 | 2.52 | 1.09 | 53.5 | 5.2 | 58.7 | 1.73 | 11.23 |
| Example 1.15. | 1.00 | 2.50 | 1.11 | 49.3 | 4.8 | 68.5 | 1.75 | 9.33 |
| Example 1.16. | 1.00 | 4.83 | 1.10 | 16.5 | 5.7 | 41.8 | 3.78 | 12.27 |
| Example 1.17. | 0.99 | 4.81 | 1.09 | 16.7 | 5.7 | 42.3 | 3.73 | 12.21 |
| Example 1.18. | 0.99 | 4.01 | 1.10 | 16.6 | 4.8 | 41.7 | 3.11 | 12.32 |
| Example 1.19. | 1.00 | 2.50 | 1.10 | 65.3 | 6.7 | 83.9 | 1.66 | 7.66 |
| Example 1.20. | 1.01 | 2.50 | 1.10 | 65.0 | 6.5 | 64.8 | 1.63 | 7.68 |

| | $T_{OIL}$ °C. | $T_{in}$ °C. | $T_{max}$ | $T_{out}$ °C. | PA conversion % | Selec. MAL % | c DIMAL % |
|---|---|---|---|---|---|---|---|
| DE3213681A1, Ex. 1.1. | | 161 | 184 | — | 99.5 | 98.1 | 0.49 |
| DE3213681A1, Ex. 1.2. | | 162 | 205 | — | >99.4 | 97.2 | <1 |
| Example 1.3. | 139.5 | 122.5 | 152.6 | 152.2 | 99.37 | 98.75 | 0.18 |
| Example 1.4. | 139.1 | 122.5 | 152.3 | 152.0 | 99.30 | 98.85 | 0.18 |
| Example 1.5. | 139.9 | 122.1 | 152.3 | 152.2 | 99.35 | 98.67 | 0.18 |
| Example 1.6. | 139.1 | 122.8 | 153.0 | 153.0 | 99.46 | 98.33 | 0.18 |
| Example 1.7. | 143.9 | 129.9 | 160.2 | 155.5 | 99.75 | 98.19 | 0.34 |
| Example 1.8. | 144.2 | 127.3 | 157.7 | 154.7 | 99.65 | 98.47 | 0.27 |
| Example 1.9. | 139.0 | 122.5 | 156.3 | 154.9 | 99.57 | 98.62 | 0.22 |
| Example 1.10. | 159.8 | 142.1 | 173.0 | 169.1 | 99.67 | 98.03 | 0.49 |
| Example 1.11. | 146.4 | 133.8 | 165.4 | 159.7 | 99.77 | 98.34 | 0.45 |
| Example 1.12. | 159.5 | 141.0 | 172.3 | 169.6 | 99.65 | 98.02 | 0.49 |
| Example 1.13. | 164.1 | 155.7 | 179.6 | 172.7 | 99.81 | 98.51 | 1.35 |
| Example 1.14. | 164.0 | 150.3 | 177.5 | 168.7 | 99.83 | 98.40 | 1.13 |
| Example 1.15. | 158.2 | 147.2 | 173.0 | 164.4 | 99.81 | 97.91 | 0.92 |
| Example 1.16. | 149.1 | 150.5 | 179.8 | 167.8 | 99.32 | 96.44 | 0.93 |
| Example 1.17. | 148.4 | 142.2 | 172.2 | 158.6 | 99.17 | 98.05 | 0.65 |
| Example 1.18. | 153.6 | 141.5 | 171.9 | 159.2 | 99.66 | 98.58 | 0.68 |
| Example 1.19. | 158.8 | 154.2 | 171.7 | 171.7 | 99.58 | 98.18 | 0.94 |
| Example 1.20. | 158.9 | 150.3 | 171.7 | 171.7 | 99.68 | 98.34 | 0.65 |

Methacrolein for the DOE synthesis can also be obtained in a batch process. Examples 1.21. to 1.25. show the preparation of methacrolein in the batch process. Due to the markedly higher DIMAL contents in the methacrolein, an intermediate purification of the methacrolein may be necessary.

Example 1.21. (Batch Process)

Propionaldehyde and formaldehyde in the form of formalin (in a molar ratio of 1:1) are initially charged in a 1 l autoclave. The autoclave, temperature-controlled by means of an oil bath, is sealed and pressurized with 40 bar of nitrogen. The contents are heated to approx. 120° C. with stirring. On reaching the target temperature. the catalyst solution composed of water, dimethylamine and acetic acid (0.07 parts dimethylamine to one part propionaldehyde, and an acid to base ratio of 1.1:1.0) is added. The water concentration in the feed was approx. 58% by weight and the loading of water with dimethylamine was 2.5% by weight. After about 20 min, the experiment is terminated and the autoclave is cooled in a stirred ice bath. The mixture is withdrawn and separated by means of phase separation into an organic and an aqueous phase. Both phases are investigated with respect to their composition. The propionaldehyde conversion is 99.8% by weight, the yield of MAL is 75.9% by weight and the DIMAL content of the methacrolein is 11.26% by weight.

Examples 1.22. to 1.24. (Batch Experiments; See Table 2)

Propionaldehyde and formaldehyde in the form of formalin (molar ratio of 1:1) are initially charged in a 0.45 l autoclave. The autoclave, temperature-controlled by means of an oil bath, is sealed and pressurized with 40 bar of nitrogen. The contents are heated to approx. 115° C. with stirring. On reaching the target temperature, the catalyst solution composed or water, dimethylamine and acetic acid is added. After the desired time, the experiment is terminated and the autoclave is cooled in a stirred ice bath. The mixture is withdrawn and separated by means of phase separation into an organic and an aqueous phase. Both phases are investigated with respect to their composition. The results are summarized in Table 2.

TABLE 2

Examples 1.22. to 1.24.

| | PA:FO mol/mol | DMA:PA mol % | ACOH:DMA mol/mol | $H_2O$ % by wt. | $DMA/H_2O$ % by wt. | Residence time min | $T_{Oil}$ °C. | X PA % by wt. | S. MAL % by wt. | c DIMAL % by wt. |
|---|---|---|---|---|---|---|---|---|---|---|
| 1.22. | 1 | 0.065 | 1.10 | 68 | 1.4 | 34 | 115 | 99.4 | 86 | 4.8 |
| 1.23. | 1 | 0.075 | 1.10 | 68 | 1.5 | 16 | 115 | 98.8 | 90 | 2.9 |
| 1.24. | 1 | 0.075 | 1.10 | 68 | 1.5 | 2 | 115 | 98.3 | 87 | 1.7 |

Example 1.25

In this batch process (Daizel Chemical Industries 1993) diethanolamine as secondary amine and oxaflic acid dihydrate as catalytic acid are used in equimolar amounts with respect to the reactants. The comparatively high proportion of catalyst makes it possible to conduct the reaction at markedly lower temperatures and with longer residence times. The catalyst mixture used can be used again for the reaction as aqueous phase.

A stirred tank is initially charged with 6 kg of water, 1274 g of diethanolamine and 1528 g of oxalic acid dihydrate. Subsequently, 974 g of formalin (37%) and 703 g of propionaldehyde are metered in. The reactants and the catalysts are used in equimolar amounts. The reaction mixture is heated to 58° C. under reflux for a period of approx. 20 min. After cooling and distillation of the phases obtained as a result, an organic phase of 850 g with a methacrolein content of approx. 91% Is obtained, corresponding to a yield of approx. 92%. The aqueous phase freed from methacrolein can be used again and has approximately the same activity as in the preceding batch.

Example 1.26

A stirred tank is initially charged with 6 kg of water, 1261 g of piperazine and 1069 g of adipic acid, Subsequently, 1177 g of formalin (37%) and 849 g of propionaldehyde are metered in. This corresponds to a molar ratio of 1:0.5:1:1. After completion of the reaction, the mixture is distilled and 982 g of an aqueous phase having a methacrolein content of 94% is obtained. This corresponds to a yield of 91%. The comparatively high proportion of catalyst makes it possible to conduct the reaction at markedly lower temperatures and with longer residence times. The catalyst mixture used is used again for the reaction as aqueous phase.

Example 2

2. Continuous Performance of a Direct Oxidative Esterification of Methacrolein to Methyl Methacrylate ("MMA") Using a Nanoparticulate Gold-Containing DOE Catalyst 2.1. Reactor, Reaction System and Design Data for the Catalyst Retention System Reactor:

A stirred tank reactor with a stirrer on top was used for the reaction. The materials used are made from conventional stainless steel in order to resist the slightly corrosive media. The reactor has a double jacket which is connected to a thermostat able to both cool and heat via its medium. The reactor lid is connected to a vapours pipe (100 mm nominal width) with a condenser. The stirred tank had an internal diameter of 400 mm and the reactor height (up to the top of the lid) was 1500 mm. The stirrer is connected to the reactor from above through the reactor lid and is equipped with special stirring elements enabling both an optimal gas dispersion (for the oxygen-containing gas; dried compressed air was used) and also optimal suspension of the particulate catalyst in the medium. A commercial stirring system is used, consisting of a primary disperser for large amounts of gas (from Ekato, Phasejet) and two stirring elements for gas/liquid mixtures having a radial conveying direction (from Ekato, Combijet), a total of three stirring elements which are fastened to the stirrer shaft. The distance of the stirring elements from the bottom of the reactor is 100 mm for the first stirring element and 400 mm for the second stirring element, and 700 mm for the third stirring element.

The gas line for supplying the oxygen-containing gas (compressed air is used) terminates directly beneath the dispersion element and ensures a uniform distribution of the gas over the reactor cross section and also a fine dispersal of the oxidation gas. Feed lines for reactants, recycle streams and auxiliaries are installed in the reactor via the reactor lid in such a way that the feed lines end far below the fill level of the reaction medium. The top of the condenser is connected via a line to a storage vessel which contains a methanolic stabilizer solution (500 ppm Tempol).

2.2. Catalyst Retention System:

The reactor is equipped with a catalyst retention system formed from mechanical filtration and sedimentation devices. The reaction solution discharged from the DOE reactors is lastly filtered through a filter candle with a retention capacity of 1 micrometer and freed from fines, larger particles covering the filter are backwashed into the reactor at regular intervals in order to largely reduce or eliminate loss of catalytically active material. The backwash medium used is the reaction solution itself or the pH-adjusted reaction solution after reaction with basic medium.

2.3. Reaction start and continuous reaction:

The reactor was filled with a mixture of methanol, water and MMA, methacrylic acid ("MAA") and dissolved Na methacrylate. Initially charging this reactor mixture achieves a more rapid attainment of the steady-state concentrations. The reactor was filled with 135 kg of this starting medium, the composition was 3% by weight MAA (at pH 7, 50% of this is present as the sodium salt), 35% by weight MMA, 5% by weight water, the rest being methanol. The fill level was approx. 85% of the reactor fill height. The reactor is additionally filled with 15 kg of catalyst, the slurry density is thus 10%-11% by weight with respect to the amount of catalyst used and the operating volume of the reaction solution. The reaction mixture is heated to 80° C. The stirrer is set to 300 rpm. The reactor is set to an operating pressure of 5 bar absolute (with nitrogen as the starting medium). After reaching the reaction temperature, 1 kg/h of air is introduced in stages, the reaction immediately commences, recognizable by the reduction in the level of methacrolein in the reactor or by the rise in the MMA concentration in the reaction mixture. The amount of air is increased in abovementioned stages until the offgas reaches an oxygen concentration of 4% by volume (the explosion limit of the DOE offgas is just under 8% by volume $O_2$ content), so that safe continuous operation is ensured. The offgas temperature of the DOE offgas after condensation of the condensable organic constituents (methanol, MAL, MMA, water and low boilers) is 2° C. NIR is used to measure and quantify the concentration of the various offgas constituents ($CO_2$, CO, oxygen, water, propene, nitrogen, methanol, acetone, methyl formate (FOME) and other low boilers that are discharged with the offgas). The offgas having a total content of volatile organic constituents of <1.5% by volume is thermally treated and combusted.

The starting material methacrolein (prepared from propanal and formalin in a continuous pressure reaction in the presence of catalytic amounts of dimethylamine/acetic acid) is continuously fed to the reactor via a metering pump, 180 mol of methacrolein are metered into the reactor per hour, with a degree of conversion of between 70-72% being established in the steady state. Over the entire run time of the continuous operation, a conversion of about 125 to 130 mol of methacrolein is determined. The reactor is operated according to this mode of operation with essentially two methacrolein feed streams, specifically the fresh methacrolein feed (~100 mol/h) and the methacrolein recycle feed (the overhead product of the MAL-methanol recycle column, or a MAL recovery column)(contains a further ~40 mol/h of MAL). The average reaction selectivity determined is 94.5 MMA with respect to converted methacrolein, 119 to 124 mol or MMA are produced per hour, the catalyst performance is thus 8.16 mol of MMA per hour and per kg of catalyst in this embodiment.

2.4. Preparation of MMA by Means of DOE, Reactor Output and Composition

Figure 2:
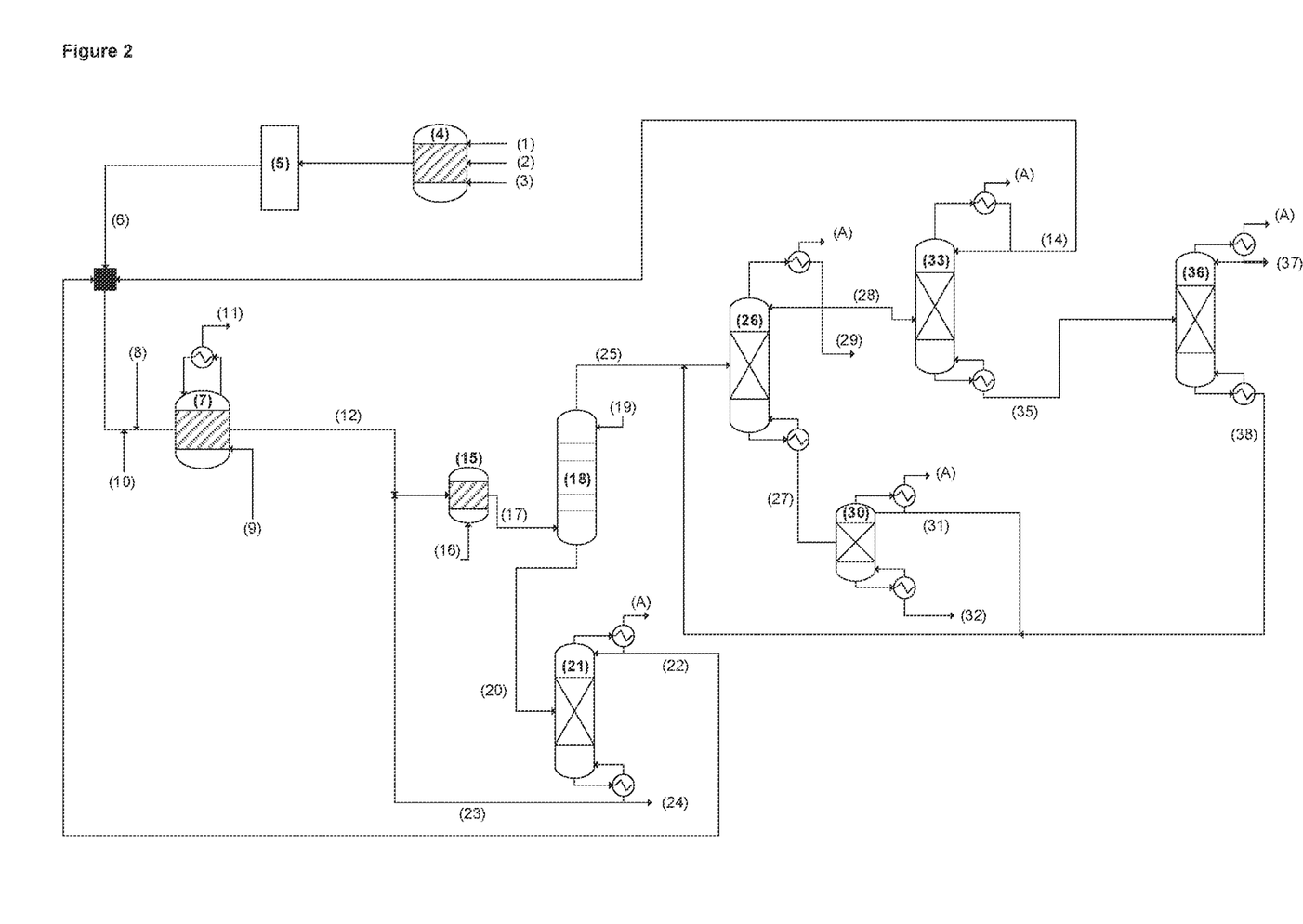
FIG. 2 shows an overall process embodiment variant and an exemplary workup sequence, without a separate methyl formate column.
Figure 4:
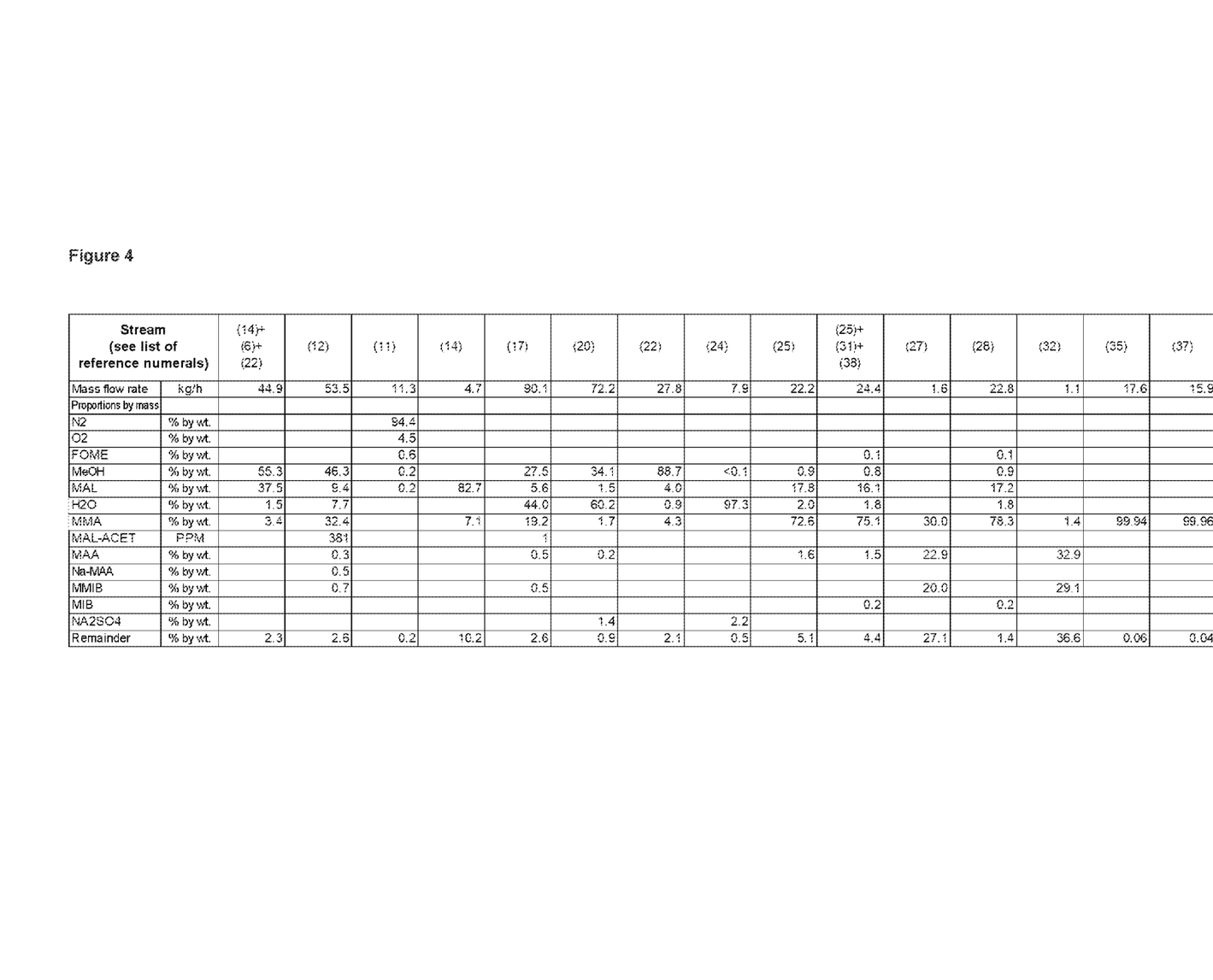
FIG. 4 shows a table of mass flow rates and compositions according to Example 2 and FIG. 2.

The continuous preparation of the feed streams, offgas composition, and product streams and the composition thereof. In the DOE reactors (7) are illustrated in FIGS. 2 and 4.

In principle, workup columns and apparatuses are equipped with an offgas system. All column tops and critical apparatus components are continuously sprayed with stabilizer solutions in order to prevent polymeric deposits. In addition, for delta-p measurements, lean air (oxygen content <6% by volume) Is used, which is fed in at the bottom of the columns.

The output of the steady-state reaction mixture via the catalyst retention system (inclined clarifier and filtration units) Is controlled via a pressure regulating valve and is on average 50 to 70 kg/h, of which 20-30 kg are recycled into the reactor after cooling and base conditioning. The output (12) to the workup sections in this exemplary experimental implementation is 45-80 kg during this operation period, there is thus an average reaction time of about 4 h. The reaction mixture is depressurized and passed via an intermediate vessel (20 l volume), with dissolved residues of gas, which would otherwise interfere with subsequent reaction and separation operations, being to a large extent removed. After cooling and depressurization in the intermediate vessel, these gas constituents have to a large extent been removed.

The composition of the continuous reactor output is continuously measured downstream of the filtration unit (polypropylene filter candle having 1 micron retention capacity) by means of NIR and the concentration of MMA and MAA and also unconverted methacrolein is additionally determined and checked using HPLC. The low-concentration organic components, for example di-methacrolein, di-methacrolein methyl ester and methacrolein dimethyl acetal (=dimethylisobutene, MAL-ACET) are determined by gas chromatography with flame ionization detector FID, water is subjected to Karl Fischer titration and additionally determined using GC on a separate port.

The composition after 24 h is:
MMA: 32.4% by weight
MeOH: 46.3% by weight
Methacrolein: 9.4% by weight
Methyl methoxyisobutyrate (MMIB): 0.7% by weight
Methacrylic acid (including Na-MAA): 0.8% by weight
Water: 7.7% by weight Offgas amounts and composition of the offgas (11) and also feed composition (fresh feed and recycle streams) are likewise Illustrated in detail in FIG. 4.

Other components present are acetals of methacrolein (MAL-ACET) at a concentration of about 400 ppm, and methyl Isobutyrate (MIB), the formal hydrogenation product or MMA, likewise at a concentration of less than 1000 ppm in the degassed product mixture, and also dimers of methacrolein and derivatives thereof.

The reaction product solution is analysed qualitatively for polymeric constituents by means of addition of methanol and, alternatively, with hexane (10 parts solvent, 1 part reaction solution), with a negative result.

2.5. Brønstedt Acid Addition, pH Adjustment and Acetal Conversion, Reactor Output and Composition Water and acid are optionally added to the DOE reaction mixture in order to hydrolyse harmful acetals. The continuous preparation of the product streams with reduced acetal content and the composition thereof downstream of the MAL acetal converter (15) are Illustrated in FIGS. 2 and 4.

In detail, 96% sulfuric acid (16) is added to the mixture until the pH of the resulting mixture is between 2 and 2.5. In addition, water is added to the degassed DOE reactor mixture; in the exemplary embodiment chosen, process water (23) from the methanol recovery column is used.

At 40° C. and with 10 min residence time, the acetals (for example methacrolein dimethyl acetal) present in a thoroughly mixed system (a 5 l stirred reactor with stirrer element on top is used) are hydrolytically cleaved. Therefore, this step achieves a reduction of the acetal content from just under 400 ppm to 1 ppm and thus a non-hazardous level for MMA monomer quality or PMMA polymer quality.

The result is a mixture (in this case biphasic, (17)) after the MAL acetal conversion, having the following composition:
MMA: 19.2% by weight
MeOH: 27.5% by weight
Methacrolein: 5.6% by weight
Methyl methoxyisobutyrate (MMIB): 0.5% by weight
Methacrylic acid: 0.5% by weight
Water: 44.0% by weight
MAL acetal: 1 ppm Further components present are dimers of methacrolein and also esters thereof and derivatives thereof (high boilers compared to MMA), and also methyl isobutyrate (MIB), the formal hydrogenation product of MMA.

This product mixture is subjected to an extraction (18). In the example chosen, the extraction was performed in a pulsed extraction column with external pulse drive and having a diameter of 120 mm and a height of 2500 mm. In the upper part of the column, 10 to 15 kg of demineralized water (19) are metered in, the introduction point is above the introduction point of the organic feed solution, 200 mm (measured from the bottom of the extraction column). The aim of the operation is the production of an organic phase containing MMA, methacrolein and methacrylic acid with as little MEOH and water as possible, and the production of an aqueous phase to a large extent containing the mineral salt formed (in the example sodium sulfate). According to our theoretical calculations, the apparatus setup selected represents 4-5 theoretical extraction stages. The extraction is performed at 40° C. and standard pressure. In the upper part of the column, a clear phase boundary forms which remains more or less mulch-free even during operation for several hundred hours. Polymeric deposits are also not observed.

The organic phase ("second phase" (25)), which is fed continuously to the following workup, has the following composition in steady state operation:
MMA: 72.6% by weight
MeOH: 0.9% by weight
Methacrolein: 17.8% by weight
Methacrylic acid: 1.6% by weight
Water: 2.0% by weight
Other organic components: 5.1% by weight The organic components in the organic phase consist of a mixture of dimers of methacrolein and derivatives thereof and also methyl methoxyisobutyrate (MMIB). According to analysis by means of ion chromatography, the organic phase is also very substantially free from sodium sulfate (<200 ppm).

The aqueous phase ("first phase" (20)), which is fed continuously to the following workup, has the following composition in steady state operation:
MMA: 1.7% by weight
MeOH: 34.1% by weight
Methacrolein: 1.5% by weight
Methacrylic acid: 0.2% by weight
Water: 60.2% by weight
Sodium sulfate: 1.4% by weight 2.6. Workup of the "First Phase", Recovery of MMA, MAL, MeOH from the Aqueous Phase The aqueous "first phase" (20) is purified of reactants and products (MeOH, MAL, MMA) by distillation. The continuous distillation and recycling of organic materials of value, and the wastewater formed, are illustrated in FIGS. 2 and 4.

In this so-called methanol recovery column (operating pressure 1 bar absolute (21)), the methanol and also residues of MMA and methacrolein are recovered after extraction. These reactants and portions of the MMA are recycled into reactor II (7) and thus enter the organic workup circuit. This operation also generates at the bottom of the distillation column process wastewater (24) which more or less contains all of the sodium sulfate from the neutralization. The distillation column is equipped with high-performance DX structured packings from Sulzer (diameter 120 mm, height 2000 mm) and is operated with a reflux ratio of 1.1 at standard pressure. Under these conditions, a temperature of about 65° C. is established at the top of the column and a bottom temperature of 104° C. is established.

Process wastewater (24) containing 2%-2.5% by weight of sodium sulfate in addition to 97.3% by weight of water accumulates at the bottom, at the top a vapour stream (22) forms with the following composition:
MMA: 4.3% by weight
MeOH: 88.7% by weight
Methacrolein: 4.0% by weight
Water: 0.9% by weight The bottom stream is sent for disposal (24), or a substream (23) can be recycled to various points in the process. This sodium sulfate/water stream (23) in the present experimental description is recycled in part to assist the extraction or into the MAL acetal converter, see FIG. 2.

2.7. High boiler column: Workup of the organic "second phase", removal of MMA, MAL and low boilers from high-boiling components The organic "second phase" (25) is subjected to a distillative separation (low boilers, MAL, MMA) from components that are relatively high boiling compared to MMA (MAA, Di-MAL and derivatives, MMIB, etc.).

The continuous distillation and pre-purification to produce crude MMA and the resulting organic high boiler stream are illustrated in FIGS. 2 and 4.

In this so-called high boiler column (26) (operating pressure 0.2 to 0.24 bar absolute), the methanol and also residues of water and more or less all of the methacrolein together with the major amount of MMA are obtained as overhead condensate (28). The overhead condensate in the case of the composition given in this experimental variant embodiment Is made up of two phases (28) and (29).

The organic phase (28) mainly contains MMA and methacrolein and small amounts of water and by-products:
MMA: 78.3% by weight
MeOH: 0.9% by weight
Methacrolein: 17.2% by weight
Water: 1.8% by weight By-products still present in small amounts are methyl formate (FOME), acetone and MIB.

This operation also generates, at the bottom of the distillation column, an organic bottom stream (27) containing residues of MMA and primarily higher-boiling methacrylic acid, MMIB and DI-MAL and derivatives. Traces of mineral salt are also entrained in this stream and are therefore separated from the crude MMA. These organic by-products can be worked up further or materials of value such as MAA can be Isolated or, in specific processes, converted into MMA (not part of the present invention).

The distillation column is equipped with high-performance DX structured packings from Sulzer (diameter 100 mm, height 2000 mm) and is operated with a reflux ratio of 1.0 at a moderate negative pressure. Under these conditions, a temperature of about 50° C. is established at the top of the column and a bottom temperature of 85° C. is established.

2.8. Workup of the Organic High Boiler Phase, Final Removal of Residual MMA, of High-Boiling Components: MMA Recovery Column The organic high boiler phase is subjected to an optional further distillative separation (30) from components that are higher boiling compared to MMA (MAA, DI-MAL and derivatives. MMIB, etc.). The organic high boiler stream (32) formed during the continuous distillation at reduced pressure (operating pressure 0.03 to 0.06 bar absolute, here 0.05 bar) is illustrated in FIGS. 2 and 4.

In principle, the distillative functions of operations 2.7 and 2.8 can be conducted in a single column with adapted pressure and temperature parameters. The distillate (31) is recycled as co-feed upstream of the high boiler column in FIG. 2.

2.9. Low Boiler Column: Workup of the Organic Distillate Phase from the High Boiler Column, Distillative Removal of Methacrolein (in the Distillate) from MMA (Bottoms Product)

The organic distillate from the high boiler column (28) is subjected to a further distillative separation (33) from components that are lower boiling compared to MMA. In principle, an MMA of high purity already accumulates here at the bottom (35) of the column, however the MMA of this variant, despite the high purity of >99% by weight, still contains some stabilizers from the preceding process stages.

In the top ((34) or (14)) of the column, substances accumulate that are low boiling in particular compared to MMA and also components which form low-boiling azeotropes together with MMA and/or MAL (binary and tertiary azeotropes). The main function of the column is to separate methacrolein from MMA in order to enable recycling of the methacrolein present into the DOE reaction.

A phase separation may optionally be performed at the top of the column in order to reduce the amount of water recycled into the DOE reaction or to achieve a reduction and discharge of undesired low boilers.

The organic low boiler distillate (14) formed during the continuous distillation at a reduced pressure of 600 mbar Is illustrated in FIGS. 2 and 4. Under these conditions, a temperature of about 53° C. results at the top and a temperature of 84° C. results at the bottom. The column diameter is 80 mm, Sulzer DX structured packings (high-performance structured packings) are installed, packing height 2000 mm.

The MAL-rich distillate (14) is recycled as co-feed into the DOE reactor section (7), FIG. 2.

2.10 MMA Purifying Column: Workup of the Organic Bottom Phase from the Low Boiler Column, Distillative Separation of Monomer-Grade MMA (in the Distillate) from Crude MMA with High Stabilizer Contents The organic bottoms of the low boiler column (35) are subjected to a further distillative separation (38) and fine purification. In principle, an MMA meeting monomer specification accumulates in the distillate (37) of the column. Crude MMA with a high stabilizer content (38) accumulates in the bottom of the column.

This highly stabilized MMA can be recycled to one or more of the preceding columns (recycling to the high boiler column (38) is illustrated by way of example. FIG. 2). As an alternative, this stream can be used as a stabilizer solution for application to the critical column tops of various separation operations.

The column is operated with a moderate vacuum of 220 mbar, a top or distillate temperature of just under 57° C. is established, with a bottom temperature of 59° C. The column diameter is 80 mm, Sulzer DX structured packings (high-performance structured packings) are installed, packing height 2000 mm. The reflux ratio is 1.0.

Figure 3:
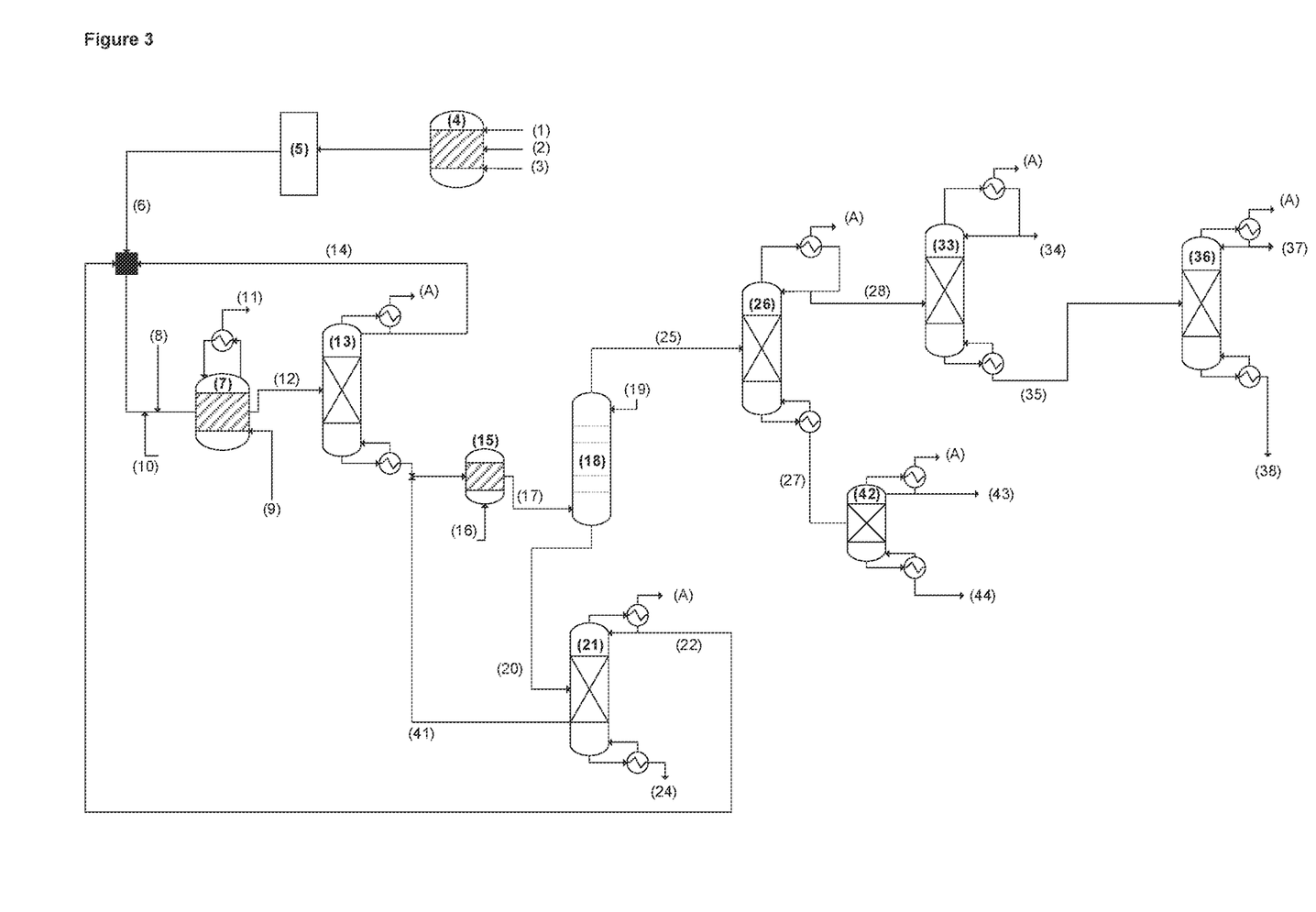
FIG. 3 shows a comparative process embodiment and an exemplary workup sequence, including an extractive workup of an MMA/methanol mixture containing methacrylic acid alkali metal salt.

Example 3 (Comparative Example According to the Prior Art, FIG. 3)

Comparative example: A preferred workup sequence in accordance with U.S. Pat. No. 10,301,251 B2 Is illustrated and intended to be briefly outlined. Details and sequence of the various separation operations are Illustrated in FIG. 3.

This comparative example represents the prior art and Is used to demonstrate the advantages of the process according to the invention with respect to the specific energy consumptions, here in particular steam and cooling water use.

Methacrolein preparation proceeding from formalin and propionaldehyde, and the workup thereof, are in principle identical ((1), (2). (3), (4), (5)). The DOE reaction ((7), (8), (9). (10)) and reaction regime per se are likewise similar, but differ in the reed composition, in particular by different recycling streams. e.g. (14), with different composition.

MAL recovery column (13): The DOE reaction output (12), consisting of methanol, unconverted methacrolein, MMA, water and alkali metal salt (or alkaline earth metal salt) of methacrylic acid, is worked up in a first distillation column (13). In this first distillation, more or less the entirety of the methacrolein, and portions of methanol, MMA and water, are taken off at the column top (14) and returned into the DOE reactor (7). The bottoms of the column contain MMA, water and methanol and also methacrylic acid and methacrylic acid salt, and high-boiling by-products.

MAL acetal conversion: With addition of acid (16) (in this example sulfuric acid), the bottom stream of the first column is subjected to acetal conversion at a pH markedly below the pH of the reaction solution in the DOE reactor. In the acetal conversion, traces of the disruptive acetal are virtually completely hydrolysed, water is optionally added. According to U.S. Pat. No. 10,301,251 B2, for example, an additional water addition is optionally Implemented via a water-containing vapours sidestream (41) from the methanol recovery column (21). This has the advantage that in addition to water, residues of methacrylic acid (which are in the wastewater) are simultaneously recycled back to the workup as well, and are therefore not lost. The product (17) from the acetal converter is sent to a multistage extraction (18) (illustrated in FIG. 3 in simplified form as a continuous extraction column).

Extraction and MeOH recovery column: The aqueous phase (20) from the extraction contains in large part methanol and small amounts of MMA. In the MeOH recovery column, these materials of value (MeOH and MMA) are recovered as overhead product (22) and are recycled into the reaction (7) or workup. An aqueous sidestream (41) containing small amounts of methacrylic acid and relatively large amounts of water is optionally taken off. The wastewater from the DOE, containing small amounts of organic impurities and more or less free from MMA, MAA and methanol, accumulates at the bottom (24). The wastewater stream contains the neutralization salt, sodium sulfate in the example chosen.

Extraction and organic phase from the extraction: the organic phase (25) from the extraction essentially consists or MMA with small amounts of methanol, water and methacrolein (incidentally a central distinguishing feature with respect to the present process according to the invention). Traces of disruptive low boilers are also present here (e.g. methyl formate), which have to be removed, and also organic high-boiling products such as dimeric methacrolein and derivatives thereof (e.g. DI-MAL methyl ester and MMIB). MMA is purified in a sequence of distillation columns such that the specifications for monomer grade can be achieved.

High boiler column (26) To this end, firstly all high-boiling components are removed in a high boiler column (26). MMA goes to the top (28) of this column, together with low boilers, or as an azeotrope with these low boilers. Methacrylic acid from the bottom stream (27) can be separated from other high boilers and isolated in an optional fractionation (illustrated in FIG. 3 as so-called "MAA column" (42)).

Low boiler column (33): The distillate from the high boiler column is worked up in the low boiler column; all low-boiling components are separated off from crude MMA (35), which accumulates in the bottom along with the process stabilizers.

MMA purifying column (36): The stabilizers are removed from on-specification MMA (as distillate (37)) in the MMA purifying column (38). This bottom stream (38) may optionally be recycled in order to minimize MMA losses.

In table 3, the specific energy consumptions of the process variant (FIG. 3, U.S. Pat. No. 10,301,251 B2) ascertained by means of simulation are compared with those of the process according to the invention (FIG. 2).

TABLE 3

Comparison of specific energy consumptions for a given identical product purity (MMA specification).

| Energies and streams for disposal | Unit | Example 3 Comparative example | Example 2 Process according to the invention |
|---|---|---|---|
| Steam | $kg_{steam}/kg_{MMA}$ | 4.95 | 4.25 |
| Cooling water | $l_{cooling\ water}/kg_{MMA}$ | 355 | 294 |

TABLE 3-continued

Comparison of specific energy consumptions for a given
identical product purity (MMA specification).

| Energies and streams for disposal | Unit | Example 3 Comparative example | Example 2 Process according to the invention |
|---|---|---|---|
| Brine | $kW_{cooling\ power}/kg_{MMA}$ | 0.19 | 0.17 |
| Organic waste | $kg_{waste}/kg_{MMA}$ | 0.08 | 0.07 |
| Wastewater | $kg_{wastewater}/kg_{MMA}$ | 0.61 | 0.50 | a. workup sequence according to Example 3 (FIG. 3)
b. workup sequence according to process according to the invention (FIG. 2).

LIST OF FIGURES AND REFERENCE NUMERALS

Figure 1:
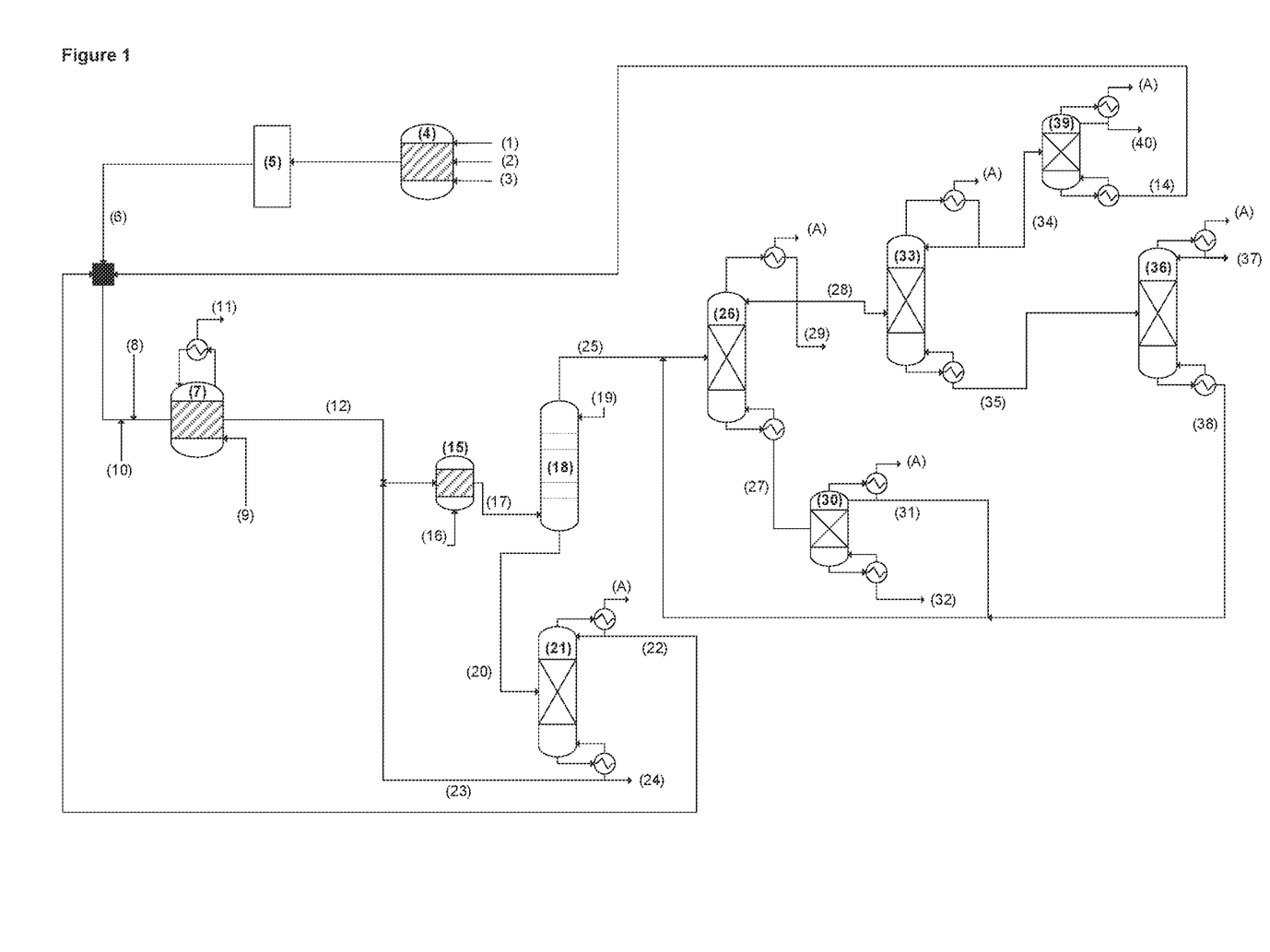
FIG. 1 shows an overall process embodiment variant and an exemplary workup sequence, including a separate methyl formate column.

The following figures are attached:

FIG. 1:
Overall process embodiment variant: PA+FA→MAL; 2.) MAL+O2+MeOH→MMA+H2O, and an exemplary workup sequence, here including a separate methyl formate column FIG. 2:
Overall process embodiment: PA+FA→MAL; 2.) MAL+O2+MeOH→MMA+H2O, and an exemplary workup sequence, here without a separate methyl formate column FIG. 3:
Comparative process according to the prior art as per U.S. Pat. No. 10,301,251 B2 (Groemping et al.) Overall process embodiment: PA+FA→MAL; 2.) MAL+O2+MeOH→MMA+H2O, and an exemplary workup sequence, with extractive workup of an MMA/methanol mixture containing methacrylic acid alkali metal salt FIG. 4:
Mass flow rates and composition according to Example 2 and FIG. 2

REFERENCE NUMERALS

Oxidative esterification of the methacrolein to afford an alkyl methacrylate and recycling of the methacrolein (1) formalin feed into reactor I
(2) propanal feed into reactor I
(3) optional stabilizer feed into reactor I
(4) reactor I for methacrolein synthesis
(5) workup of the crude methacrolein
(6) methacrolein feed into reactor II
(7) reactor II for oxidative esterification of the methacrolein
(8) alcohol feed (generally methanol feed)
(9) oxygen/air feed
(10) base feed
(11) reactor II offgas
(12) reactor II reactor output
(13) distillation column MAL recovery column (comparative example, FIG. 3, only)
(14) MAL recycle
(15) optional mixer/MAL acetal converter
(16) acid feed (generally sulfuric acid)
(17) MAL acetal converter product stream
(18) extraction
(19) water feed for extraction
(20) aqueous phase extraction, "first phase"
(21) methanol recovery column
(22) low-boiling fraction containing alcohol for return to reactor II
(23) optional bottoms fraction, recycle of methanol recovery column
(24) bottoms fraction containing water, acid and the alkali metal salts thereof for disposal or further workup
(25) organic phase from the extraction, "second phase"
(26) high boiler column for removal of high boilers
(27) bottoms fraction ("third phase"), containing MMA, methacrylic acid and high boilers
(28) distillate ("fourth phase"), containing MMA and low boilers
(29) aqueous phase distillate from the high boiler column
(30) MMA recovery column
(31) distillate from the MMA recovery column, containing MMA, for recycling into the high boiler column
(32) bottoms fraction from the MMA recovery column, containing methacrylic acid and high boilers
(33) low boiler column for removal of low boilers
(34) distillate from the low boiler column, containing low boilers (variant 1 (FIG. 1) and comparative example (FIG. 3))
(35) bottoms fraction from the low boiler column, containing MMA purified of low boilers
(36) MMA purifying column for final purification of the MMA
(37) on-specification MMA as distillate from the MMA purifying column
(38) bottoms fraction from the MMA purifying column, optional recycle to the high boiler column
(39) methyl formate column (variant 1, FIG. 1, only)
(40) methyl formate column distillate, containing low boilers, for example methyl formate
(41) optional methanol recovery column sidestream (comparative example, FIG. 3, only)
(42) MAA column (comparative example, FIG. 3, only)
(43) MAA column distillate, containing methacrylic acid (comparative example, FIG. 3, only)
(44) bottoms fraction from the MAA column, containing high boilers (comparative example, FIG. 3, only)
(A) offgas

The invention claimed is:
1. A process for preparing alkyl methacrylates, comprising:
preparing methacrolein in a first reaction stage in a reactor I, and
oxidatively esterifying the methacrolein in a second reaction stage in a reactor II with an alcohol in a liquid phase, to give an alkyl methacrylate,
wherein a reactor output from reactor II is separated into a first aqueous phase, containing more than 80% by weight of alcohol present in the reactor output, and a second phase, containing more than 80% by weight in each case of the alkyl methacrylate and methacrolein (MAL) present in the reactor output, and wherein the second phase is worked up in a subsequent single- or multi-stage distillation in such a way that methacrolein is separated from alkyl methacrylate.

2. The process according to claim 1, wherein the second phase contains more than 90% by weight in each case of the alkyl methacrylate and methacrolein (MAL) present in the reactor output, and wherein the second phase is worked up in such a way that:
   a. first the alkyl methacrylate and the methacrolein are separated off from high-boiling components by distillation, and subsequently methacrolein is separated off by distillation from relatively higher-boiling alkyl methacrylate, or
   b. first the alkyl methacrylate and the high-boiling components are separated off from methacrolein by distillation, and subsequently alkyl methacrylate is separated off by distillation from components that are high-boiling relative to the alkyl methacrylate,
   before alkyl methacrylate is obtained in monomer quality as an overhead product in a final distillation.

3. The process according to claim 1, wherein the alcohol is methanol and the alkyl methacrylate is MMA.

4. The process according to claim 1, wherein the second phase is separated into a third phase containing high-boiling components and a fourth phase containing more than 90% by weight in each case of the alkyl methacrylate and the methacrolein (MAL) present in the reactor output, and wherein the fourth phase is first separated in a phase separator from at least 90% by weight of water present in the fourth phase, before a predominant portion of the alkyl methacrylate is separated from a predominant portion of the MAL in a distillation column.

5. The process according to claim 1, wherein the second phase is separated into a third phase containing high-boiling components and a fourth phase containing more than 90% by weight in each case of the alkyl methacrylate and the methacrolein (MAL) present in the reactor output, and wherein the fourth phase or an organic phase of the fourth phase, after separation from an aqueous phase in a phase separator, is separated in a distillation column into a low-boiling fraction, containing at least 60% by weight of the MAL from the reactor output, and a high-boiling phase, containing at least 90% by weight of MMA from the reactor output.

6. The process according to claim 4, wherein a low-boiling MAL-containing fraction is separated from low-boiling constituents in a further column, and a high-boiling fraction of the further column, containing at least 60% by weight of the MAL from the reactor output, is passed into reactor II or into a mixer or heat exchanger connected upstream of reactor II.

7. The process according to claim 5, wherein a MAL-containing fraction of the fourth phase is first separated from the aqueous phase in the phase separator, prior to the separation in a distillation column of low-boiling constituents and transfer of a MAL fraction into or upstream of the reactor II.

8. The process according to claim 1, wherein the reactor output from reactor II is first admixed in a converter with a strong acid and optionally additional water, prior to the separating of the first phase from the second phase, and wherein the first phase is separated in a further distillation column into a phase predominantly containing alcohol and a high-boiling phase, which is disposed of.

9. The process according to claim 8, wherein an amount of the strong acid added is such that a pH during the separating of the first phase from the second phase is always ≥1 and less than 5.

10. The process according to claim 2, comprising the step a.

11. The process according to claim 2, comprising the step b.

12. The process according to claim 2, wherein the alcohol is methanol, and the alkyl methacrylate is MMA.

13. The process according to claim 8, wherein the water is added.

14. The process according to claim 4, wherein the alcohol is methanol, and the alkyl methacrylate is MMA.

15. The process according to claim 1, wherein the second phase contains more than 90% by weight in each case of the alkyl methacrylate and methacrolein (MAL) present in the reactor output.

16. The process according to claim 15, wherein the alcohol is methanol, and the alkyl methacrylate is MMA.

* * * * *